Dec. 4, 1934. W. EASLEA Plant Pat. 114
ROSE
Filed July 2, 1934
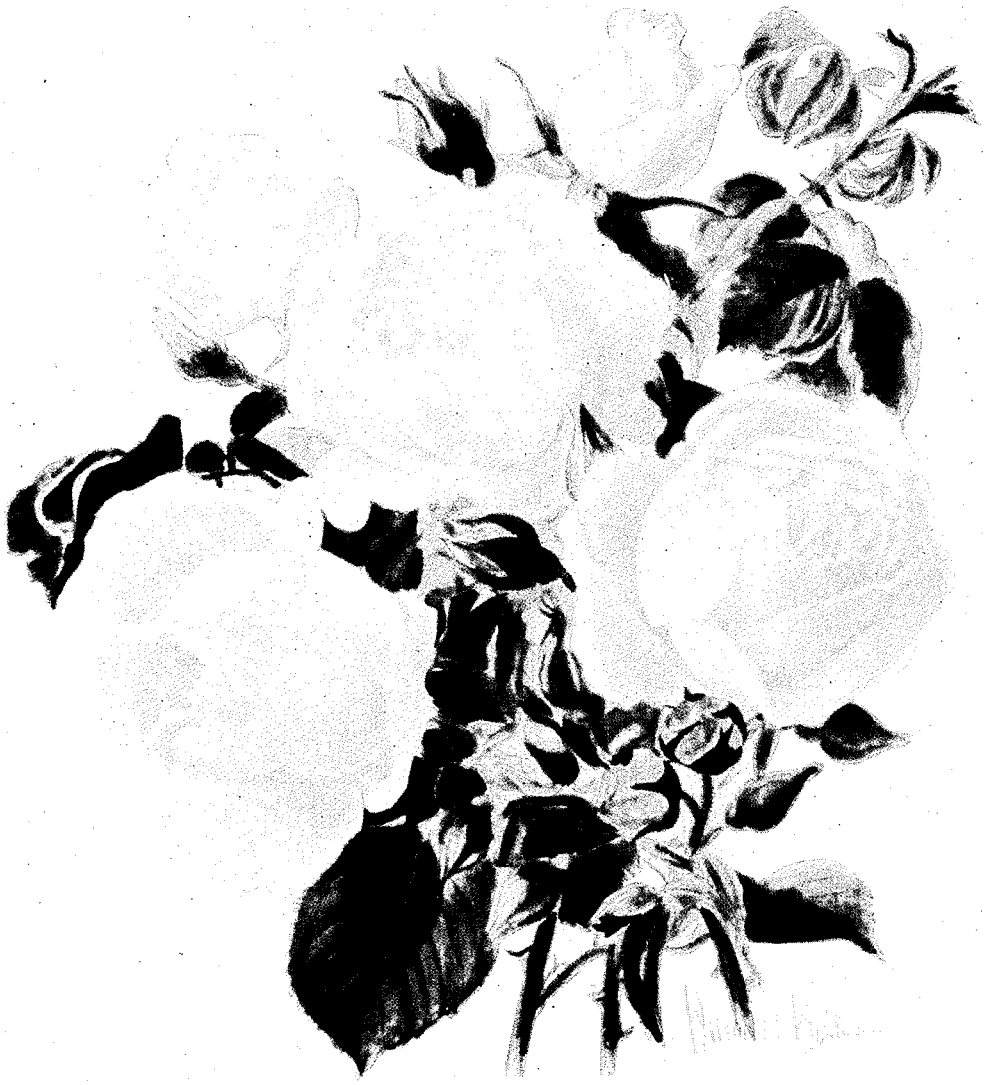
Inventor
Walter Easlea
By Orville M Kile
Plant Patent Agent Patented Dec. 4, 1934

Plant Pat. 114

UNITED STATES PATENT OFFICE

114

ROSE

Walter Easlea, Leigh-on-Sea, England, assignor to Charles H. Totty, Madison, N. J.

Application July 2, 1934, Serial No. 733,527

1 Claim. (Cl. 47—61)

My present invention relates to improvements in climbing or rambler roses of a predominantly yellow color. The object of my improvements are, briefly, to provide a new variety of rose of the type mentioned having large, full blossoms of hybrid-tea character, in beautiful yellow and salmon color tones; being a vigorous grower and heavy bloomer; having pleasing foliage color combinations, and other desirable characteristics.

This new variety of rose is the result of definite breeding work carried on by myself and is a Hybrid Wichuraiana.

The accompanying illustration shows in full color buds in various stages of development, the opened flower, and the foliage,—all depicted as nearly as possible in their true forms and colors. It must be understood, however, that there will be some variations, particularly as to color tones, when this variety is grown under different conditions of soil and climate.

The following is a detailed description of this variety of rose:

*The plant* is a hardy, vigorous grower and blossoms profusely. The abundant bright green foliage with coppery tinted new or flowering wood and leaves, together with the chrome yellow flowers and buds having touches of red or pink, makes a most striking and pleasing combination.

*Stems* are medium thickness for rambler type of rose, reddish in color—particularly the new flowering wood—and are beset with rather large thorns also reddish in color. There are no thorns on the peduncle but a moderate number of reddish hairs. Usually two or three flowers or buds arise from the same point on the stem but in some cases individual flowers occur with stems five to seven inches long.

*Leaf branches* consist ordinarily of five leaflets set on a rachis having two or three small thorns on the under side.

*Leaves* are abundant in quantity, approximately "forest green" in color (Ridgway's Color Standards and Nomenclature, Plate XVII), glossy, medium to small, leathery in texture, and have rather deeply serrated edges.

*Stipules* are medium sized, terminating in long, slender, non-curling tips.

*Hips* are tapering rather than abrupt.

*Buds* are ovoid in form and terminate in long points. As the bud swells it becomes more nearly globular and when it begins to open the tips show reddish and lemon chrome colors (Ridgway's Color Standards and Nomenclature, Plate IV). The number of buds to a cluster vary from 4 to 15.

*Sepals*. Five in number, regular in shape, about one inch long, and not given to foliaceous development. One or more of the sepals on each bud usually bears some reddish-brown coloring either near the base or at the extreme tips.

*Blossoms* are large and full for a rambler rose, often measuring up to four inches in diameter and having 30 to 40 petals. They are of the hybrid tea type, last well and are intensely fragrant. When in their prime they are cup shaped with full centers, opening later to expose the long yellow stamens.

As the bud opens and the sepals turn back there is usually a streak of pink or crimson visible running up the middle of one of the outer petals. These outer petals soon turn back, however, so that the crimson streak does not show.

The coloring of the opened flower resembles that of the variety Mrs. Wemyss Quin—that is, principally lemon chrome but washed with maddery orange. Some petals are a lighter yellow than lemon chrome and the inside of the outer row of petals often shows a slight pink wash or blush. The inside surfaces of the central petals are darker in tone and may be described as "light cadmium." There is some variation as between blossoms, particularly in that the inside petals sometimes have a salmon color.

The stamens are long, yellow and mounted by medium sized buff colored anthers. The pistils are white with yellowish tops. While the stamens are numerous the pistils are relatively few and quite well developed. There may be not more than 15 pistils in a flower, while the stamens may number a hundred or more.

Having thus disclosed my invention, what I claim as new is:

The variety of climbing rose herein shown and described, characterized particularly by its vigorous growth and heavy production of yellow toned, full petaled, fragrant blossoms as described, and by the reddish or coppery colored new growth of leaves and stems.

WALTER EASLEA.